(12) United States Patent
Bhalachandra Dharmadhikari et al.

(10) Patent No.: US 8,470,367 B2
(45) Date of Patent: *Jun. 25, 2013

(54) ORAL DRUG DELIVERY SYSTEM

(75) Inventors: Nitin Bhalachandra Dharmadhikari, Mumbai (IN); Yashoraj Rupsinh Zala, Mumbai (IN); Amarjit Singh, Mumbai (IN)

(73) Assignee: Sun Pharma Advanced Research Company Ltd., Andheri (E), Mumbai ( * ) Notice: Subject to any disclaimer, the term of this patent is extended or adjusted under 35 U.S.C. 154(b) by 1303 days.

This patent is subject to a terminal disclaimer.

(21) Appl. No.: 11/946,575

(22) Filed: Nov. 28, 2007

(65) Prior Publication Data

US 2008/0138410 A1 Jun. 12, 2008

Related U.S. Application Data

(63) Continuation-in-part of application No. 10/572,502, filed on Mar. 17, 2006, now Pat. No. 8,163,306.

(30) Foreign Application Priority Data

Sep. 19, 2003 (IN) .......................... 987/MUM/2003

(51) Int. Cl.
 *A61K 9/24* (2006.01)

(52) U.S. Cl.
 USPC ........................ 424/472; 424/464; 424/465

(58) Field of Classification Search
 USPC ................................................ 424/465–489
 See application file for complete search history.

(56) References Cited

U.S. PATENT DOCUMENTS

| | | | |
|---|---|---|---|
| 4,693,896 A * | 9/1987 | Wheatley et al. | 424/480 |
| 4,839,177 A | 6/1989 | Colombo et al. | |
| 5,271,946 A | 12/1993 | Hettche | |
| 5,422,123 A | 6/1995 | Conte et al. | |
| 5,593,694 A * | 1/1997 | Hayashida et al. | 424/468 |
| 5,650,169 A | 7/1997 | Conte et al. | |
| 5,681,584 A | 10/1997 | Savastano et al. | |
| 6,294,200 B1 * | 9/2001 | Conte et al. | 424/472 |
| 6,322,819 B1 | 11/2001 | Burnside et al. | |
| 6,720,005 B1 | 4/2004 | Ayres | |
| 6,733,784 B1 | 5/2004 | Ayres | |
| 7,195,778 B2 | 3/2007 | Fleshner-Barak et al. | |
| 8,163,306 B2 | 4/2012 | Dharmadhikari et al. | |
| 2005/0008701 A1 | 1/2005 | Sriwongjanva et al. | |
| 2005/0095295 A1 | 5/2005 | Maggi et al. | |
| 2005/0163845 A1 | 7/2005 | Conte | |
| 2006/0210633 A1 | 9/2006 | Dharmadhikari et al. | |
| 2007/0071816 A1 | 3/2007 | Dharmadhikari et al. | |

FOREIGN PATENT DOCUMENTS

| GB | 2140687 A | 12/1984 |
|---|---|---|
| WO | WO-2004108067 A2 | 12/2004 |

OTHER PUBLICATIONS

"U.S. Appl. No. 10/572,502, Examiner Interview Summary mailed Mar. 11, 2010", 4 pgs.
"U.S. Appl. No. 10/572,502, Final Office Action mailed Jul. 26, 2010", 8 pgs.
"U.S. Appl. No. 10/572,502, Non Final Office Action mailed Apr. 6, 2011", 8 pgs.
"U.S. Appl. No. 10/572,502, Non-Final Office Action mailed Sep. 29, 2009", 9 pgs.
"U.S. Appl. No. 10/572,502, Preliminary Amendment Mar. 17, 2006", 9 pgs.
"U.S. Appl. No. 10/572,502, Response filed Mar. 19, 2010 to Non Final Office Action mailed Sep. 29, 2009", 17 pgs.
"U.S. Appl. No. 10/572,502, Response filed Sep. 29, 2010 to Final Office Action mailed Jul. 26, 2010", 20 pgs.
"U.S. Appl. No. 10/572,502 , Response filed Feb. 1, 2012 to Final Office Action mailed Sep. 6, 2011", 22 pgs.
"U.S. Appl. No. 10/572,502, Notice of Allowance mailed Feb. 13, 2012", 5 pgs.
"U.S. Appl. No. 13/608,712, Preliminary Amendment filed Oct. 18, 2012", 7 pgs.
"U.S. Appl. No. 10/572,502, Examiner Interview Summary mailed Dec. 23, 2011", 3 pgs.
"U.S. Appl. No. 10/572,502, Final Office Action mailed Sep. 6, 2011", 10 pgs.
"U.S. Appl. No. 10/572,502, Response filed Jun. 17, 2011 to Non Final Office Action mailed Apr. 6, 2011", 16 pgs.

\* cited by examiner

*Primary Examiner* — Michael G Hartley
*Assistant Examiner* — Micah-Paul Young
(74) *Attorney, Agent, or Firm* — Schwegman Lundberg & Woessner, P.A.

(57) ABSTRACT

An oral drug delivery system comprising a coated tablet having one or more surfaces. The coated tablet further comprises a core and a coating surrounding the core. The core comprises an active ingredient composition comprising at least one active ingredient and a pharmaceutically acceptable excipient and a composition selected from a swellable composition and a reactive composition located in an immediate vicinity of one or more preselected surfaces. The coating comprising water insoluble polymer(s) and leachable component(s) is operable to be reliably removed fully from the one or more of the preselected surfaces of the tablet upon contact with an aqueous environment, but not removed from at least one of the surfaces.

16 Claims, 3 Drawing Sheets

ORAL DRUG DELIVERY SYSTEM

CROSS REFERENCE

This application is a continuation-in-part of U.S. patent application Ser. No. 10/572,502 filed on Mar. 17, 2006 now U.S. Pat. No. 8,163,306, the contents of which are incorporated by reference.

FIELD OF THE INVENTION

The present invention relates to an oral drug delivery system comprising a coating that is reliably removed fully or partially from one or more preselected surfaces of the system upon contact of the system with an aqueous environment.

BACKGROUND OF THE INVENTION

Oral administration of a drug provides a plasma level time profile of a drug or its active or inactive metabolite, which can be modulated by the design of the drug delivery system or dosage form.

Drug delivery system or dosage forms have been designed in various ways, depending on the requirements of the therapy or the needs of the patient. For example, the formulations may be designed to include a coating for the purpose of protecting the drug from the environment or prevent the release in the oral cavity and interaction of the drug with taste buds and yet release the drug instantly and rapidly in the stomach by dissolution of the coating in the gastric fluid. Instant and rapid release of the drug enables quick onset of action. These systems depend on pH-dependent coatings, which will not dissolve in the salivary fluids but dissolve readily in the gastric fluids. However, systems that depend on pH-independent coatings but can perform the same function are not available.

Drug delivery systems releasing the drug slowly over longer duration have been traditionally used to improve therapy by
- improving patient compliance to dosage regimens through the decrease in the number of doses the patient has to take in a day, by providing desired effective plasma levels for therapeutic efficacy over the duration of therapy for example throughout the day including at night when the patient is asleep;
- decreasing peak plasma levels when they are associated with side effects;
- reducing side effects in chronic therapy by reducing the fluctuation in plasma levels seen after multiple dosing of conventional rapid release systems;
- when the drug has local action on the gastrointestinal mucosa, to spread the release spatially over the whole of the gastrointestinal mucosa as the drug delivery system is transported in the mucosa by the motility of the gastrointestinal tract.

Drug delivery systems are also designed to release the drug at specific site in the gastrointestinal tract by use of pH-dependent coatings that dissolve in the pH environment at the specific gastrointestinal site. There is a need for designing cores for such coated systems wherein the cores provide rapid release without substantial delay over the specific site or region, for example a release initiated over a period of 1 minute to 30 minutes after encountering the particular site or pH. There is also a need for designing cores for such site-specific coated systems wherein the cores are designed to provide controlled release over the specific region, for example from the colon to the rectum.

We have designed novel core coated oral drug delivery systems that utilize novel technology for reliably removing the coating fully or partially from one or more preselected surfaces of the system upon contact with an aqueous environment. This novel technology can be gainfully employed in any of the above-described drug delivery systems to meet specific objectives of therapy.

U.S. Pat. No. 4,839,177 (the '177 patent) discloses a system for controlled-rate release of active substances consisting of (a) a deposit core of a defined geometric form, comprising a polymeric material having a high degree of swelling and a gellable polymeric material, and (b) a support platform consisting of a polymeric material insoluble in aqueous fluids applied to the deposit core such that it partially coats the deposit core. The trademark, Geomatrix®, refers to this system. The disadvantage of this system is that the rigid support platform can crack or flake before the active substance is completely released. U.S. Pat. No. 5,422,123 is an improvement over the '177 patent in that the support platform consists of polymer substances, which are slowly soluble and/or gellable in aqueous fluids, and plasticisers, such that the support platform does not crack or flake before the drug is completely released from the deposit core. Although the patents disclose systems wherein surface area of release is reduced by covering two or more surfaces of the deposit core, in practice such systems are difficult to manufacture at an industrial scale—especially systems wherein two lateral surfaces and one planar surface are coated by the support platform. For example, in example 2 of the '177 patent, the barrier layers were applied by immersing the core in a polymeric solution as far as the edge of its upper base, such that two lateral sides and one planar surface of the core are coated. In example 3 of the '177 patent, the barrier layers were coated on the lateral sides of the core by spraying or brushing the polymeric solution onto the sides. These methods, although possible on small experimental scale, are not feasible and reproducible on an industrial scale.

U.S. Pat. No. 5,650,169 provides a pharmaceutical tablet capable of releasing the active ingredients contained therein at subsequent times, the tablet being prepared by a process wherein a three-layered tablet core comprising a first drug-containing layer, an intermediate barrier layer and a third drug-containing layer are covered with an impermeable polymeric film. The first layer presents a raised top, which is removed by abrasion so as to allow contact of the abraded first layer surface with the environment. The composition of the barrier layer is designed to modulate release from the third layer of the tablet. A major disadvantage of this system is that it requires removal of the raised top layer by abrasion to provide a means for release of the components of the system. This may not be feasible at an industrial scale. Further, if the abrasion is not uniform, the release of the active ingredients will be affected.

U.S. Pat. Nos. 6,720,005 and 6,733,784 relate to coated, platform-generating tablets. The tablet hydrates and expands upon swallowing such that the membrane covering the coating ruptures mostly around the belly-band surface of the tablet due to swelling of the core, thereby exposing the belly surface of the core tablet to hydrating and eroding liquids. A disadvantage of the system is that the coating is not reliably removed from the belly-band surface always but may rupture at a different weak point. Thus, the surface area of exposure may vary. Also, the systems show a lag time of release of half an hour or more. Many shapes of the core have been suggested in the invention but some of these may accentuate the problems encountered during tablet manufacture. Also, the belly-band surface, which is exposed after the coating ruptures, has the least surface area and other more preferred surfaces are not exposed.

OBJECT OF THE INVENTION

It is an object of the present invention to design a coated oral drug delivery system in a manner such that the coating is reliably removed fully or partially from one or more preselected surfaces of the system upon contact of the system with an aqueous environment, provided further that the coating is not removed from at least one of the surfaces.

It is an object of the present invention to provide the aforesaid oral drug delivery system, which is designed to provide controlled release of the active ingredient contained therein.

It is another object of the present invention to provide an oral drug delivery system that provides zero-order controlled release while achieving the aforesaid objectives.

It is another object of the present invention to provide an oral drug delivery system to protect the active ingredient contained therein with a coating, and wherein the coating is ruptured upon contact with surrounding aqueous environment, permitting the instant and rapid release of the active ingredient.

It is a further object of the present invention to provide an oral drug delivery system that achieves the aforesaid objectives at a defined pH.

It is yet another objective of the present invention to provide an oral drug delivery system, which is easy to manufacture.

SUMMARY OF THE INVENTION

The present invention provides coated oral drug delivery systems using novel technology for removing coatings upon contact with an aqueous environment. Various embodiments are summarized below.

(i) An embodiment of the present invention provides an oral drug delivery system comprising—
 a. a core comprising an active ingredient composition comprising at least one active ingredient and a pharmaceutically acceptable excipient, and
 b. a coating surrounding the core,
wherein the drug delivery system is designed in a manner such that the coating is reliably removed fully or partially from one or more preselected surfaces of the system upon contact with an aqueous environment, provided further that the coating is not removed from at least one of the surfaces.

(ii) An embodiment of the present invention provides an oral drug delivery system comprising—
 a. a core comprising an active ingredient composition comprising at least one active ingredient and a pharmaceutically acceptable excipient, and
 b. a coating surrounding the core,
wherein the oral drug delivery system is in the form of a coated tablet and includes a feature such that the coating is removed partially or fully from one or more of the tablet surfaces upon contact with an aqueous environment, further wherein the feature is such that it enables the selection of any of the tablet surface or surfaces from which the coating is desired to be partially or fully removed, provided further that the coating is not removed from at least one of the surfaces.

(iii) An embodiment of the present invention as described in (ii) above wherein the feature is included in the coating or the core or both.

(iv) An embodiment of the present invention as described in (iii) above wherein the feature is that the coating on selected surface or surfaces of the tablet is selected from defective coatings and reactive coatings.

(v) An embodiment of the present invention as described in (iii) above wherein the feature is that the coating on selected surface or surfaces of the tablet includes one or more passageways in the coating on the selected surfaces.

(vi) An embodiment of the present invention as described in (iii) above wherein the feature is that the core comprises a composition selected from a swellable composition and a reactive core composition.

(vii) An embodiment of the present invention as described in (vi) above wherein the feature is located in the immediate vicinity of one or more selected surfaces of the tablet.

(viii) An embodiment of the present invention as described in (v) above, wherein the coating is impermeable to the active ingredient.

(ix) An embodiment of the present invention as described in (i) above, wherein the active ingredient composition is a swellable composition.

(x) An embodiment of the present invention as described in (i) above, wherein the core comprises an active ingredient composition and a swellable composition.

(xi) An embodiment of the present invention as described in (x) above, wherein the active ingredient composition is present as one or more layers and the swellable composition is present as one or more layers.

(xii) An embodiment of the present invention as described in (xi) above, wherein the active ingredient present in the different layers may be the same or different.

(xiii) An embodiment of the present invention as described in (i) above, wherein the active ingredient composition is a controlled release composition.

(xiv) An embodiment of the present invention as described in (xi) above, wherein one active ingredient composition is a rapid releasing composition and the second active ingredient composition containing the same active ingredient as the first active ingredient composition is a controlled release composition.

(xv) An embodiment of the present invention as described in (x) above, wherein the swellable composition comprises a swelling agent.

(xvi) An embodiment of the present invention as described in (xv) above, wherein the swelling agent is selected from the group comprising a swellable excipient, a gas generating agent and mixtures thereof.

(xvii) An embodiment of the present invention as described in (x) above, wherein the swellable composition comprises wicking agents.

(xviii) An embodiment of the present invention as described in (x) above, wherein the swellable composition comprises osmogents.

(xix) An embodiment of the present invention provides an oral controlled drug delivery system comprising—
 a. a core comprising an active ingredient composition comprising at least one active ingredient and pharmaceutically acceptable excipients,
 b. a coating surrounding the core, and
 c. a passageway in the coating,
wherein the oral drug delivery system is designed in a manner such that the coating is removed partially upon contact of the system with an aqueous environment allowing the active ingredient release to occur from the partially exposed surface.

(xx) An embodiment of the present invention provides an oral drug delivery system comprising—
 a. a core comprising an active ingredient composition comprising at least one active ingredient and pharmaceutically acceptable excipients, and b. a coating surrounding the core, wherein the oral drug delivery system has only one surface and the system is designed in a manner such that the coating is removed partially from the surface upon contact of the system with an aqueous environment.

(xxi) An embodiment of the present invention provides an oral drug delivery system comprising— a. a core comprising an active ingredient composition comprising at least one active ingredient and pharmaceutically acceptable excipients, and b. a coating surrounding the core wherein the oral drug delivery system has at least two surfaces and is designed in a manner such that the coating is removed partially from one of the surfaces when the oral drug delivery system contacts an aqueous environment, and further wherein the coating is removed from the surface different from the one having the least surface area.

(xxii) An embodiment of the present invention as described in (i) above wherein the drug release is initiated without a substantial delay after the oral drug delivery system contacts an aqueous environment.

(xxiii) An embodiment of the present invention as described in (i) above further comprising an outer coating of a pH-dependent polymer.

(xxiv) An embodiment of the present invention provides a method of isolating an active ingredient from its environment by providing an oral drug delivery system comprising— a. a core comprising an active ingredient composition comprising at least one active ingredient and pharmaceutically acceptable excipients, and b. a coating surrounding the core wherein the system has a feature such that upon contact with an aqueous environment the coating ruptures to provide instant and rapid release of the active ingredient.

BRIEF DESCRIPTION OF THE FIGURES

FIG. 1 is a diagrammatic representation of an embodiment of the oral drug delivery system of the present invention wherein the coating has a passageway.

FIG. 2 is a diagrammatic representation of an embodiment of the present invention wherein the coating does not have a passageway.

Figure 1A:
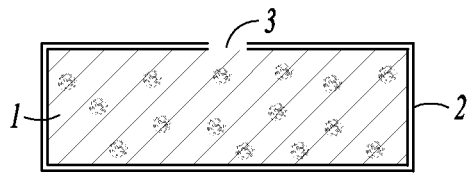
FIG. 1(a) is a diagrammatic representation of an embodiment of the oral drug delivery system of the present invention comprising a core (1) comprising an active ingredient composition, which is surrounded by a coating (2) having a passageway (3) therein.
Figure 1B:
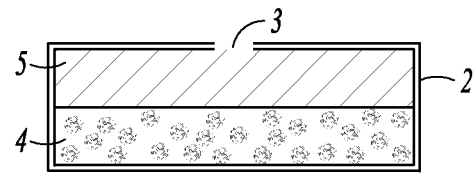
FIG. 1(b) is a diagrammatic representation of the present invention comprising a core comprising an active ingredient composition (4) and a swellable composition (5), the core being surrounded by a coating (2) having a passageway (3) therein.
Figure 1C:
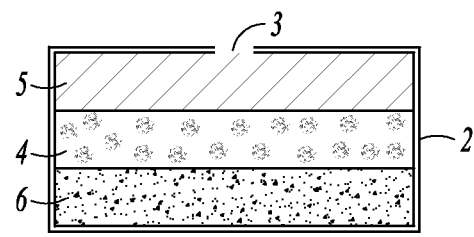
FIG. 1(c) is a diagrammatic representation of the present invention comprising a core comprising an active ingredient composition (4) and two swellable compositions (5 & 6) on either side of the active ingredient composition, so as to form a trilayered core, the core being surrounded by a coating (2) having a passageway (3) therein. The swellable compositions may or may not comprise an active ingredient.
Figure 2A:
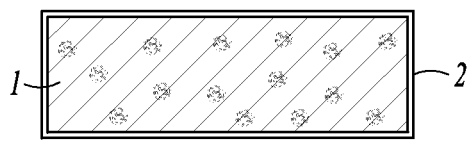
FIG. 2(a) is a diagrammatic representation of one embodiment of the present invention comprising a core comprising an active ingredient composition (1) surrounded by a coating (2).
Figure 2B:
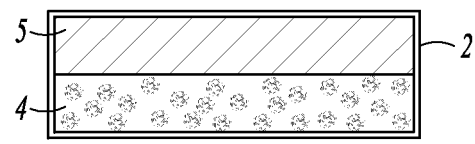
FIG. 2(b) is a diagrammatic representation of one embodiment of the present invention comprising a core comprising an active ingredient composition (4) and a swellable composition (5), the core being surrounded by a coating (2).
Figure 2C:
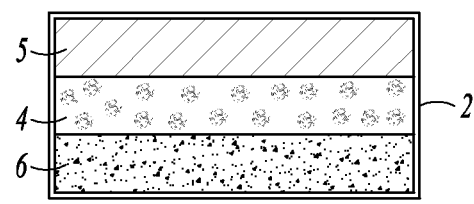
FIG. 2(c) is a diagrammatic representation of one embodiment of the present invention comprising a core comprising an active ingredient composition (4) and two swellable compositions (5 & 6) on either side of the active ingredient composition, so as to form a trilayered core, the core being surrounded by a coating (2). The swellable compositions may or may not comprise an active ingredient.

Further embodiments of the oral drug delivery systems of the present invention are not all illustrated herein. For example, further embodiments wherein any of the systems illustrated in FIGS. 1 and 2 may be further surrounded by an outer coating of a pH-dependent polymer, are not represented herein.

Figure 3:
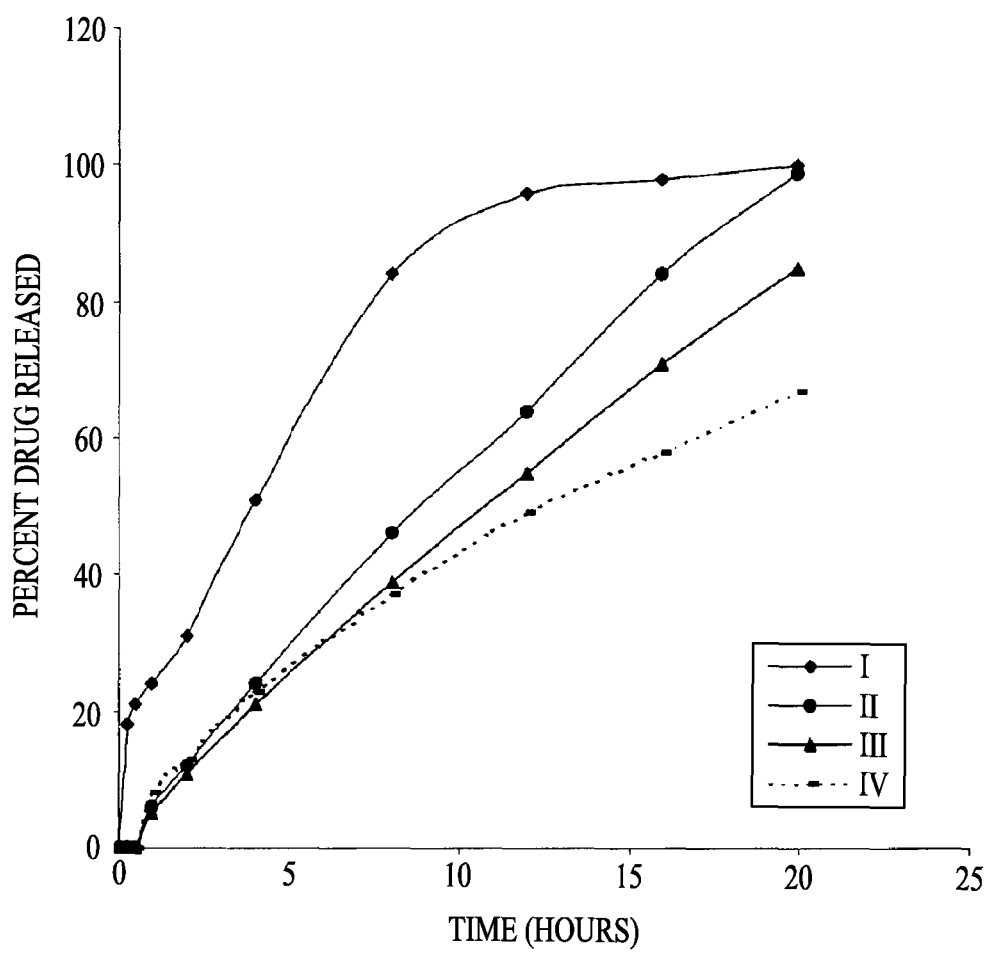

FIG. 3 is a graph showing percent drug (metoprolol) released versus time from formulations of Formulae I, II, III and IV of Example 1.

Figure 4:
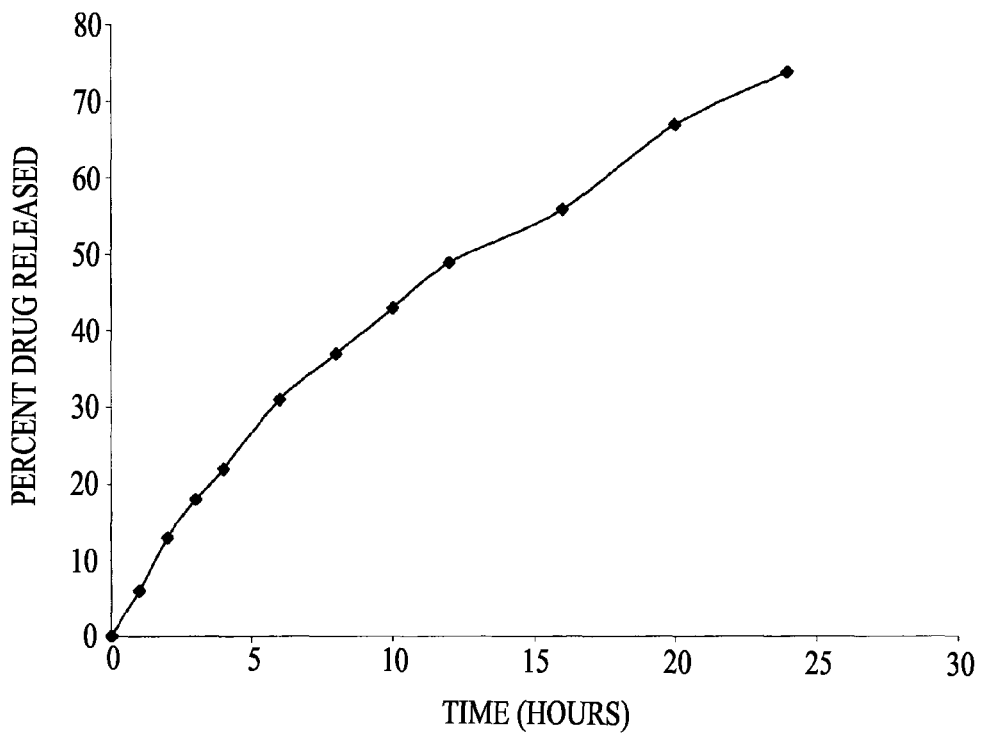

FIG. 4 is a graph showing percent drug (bupropion) released versus time from formulation of Example 2.

Figure 5:
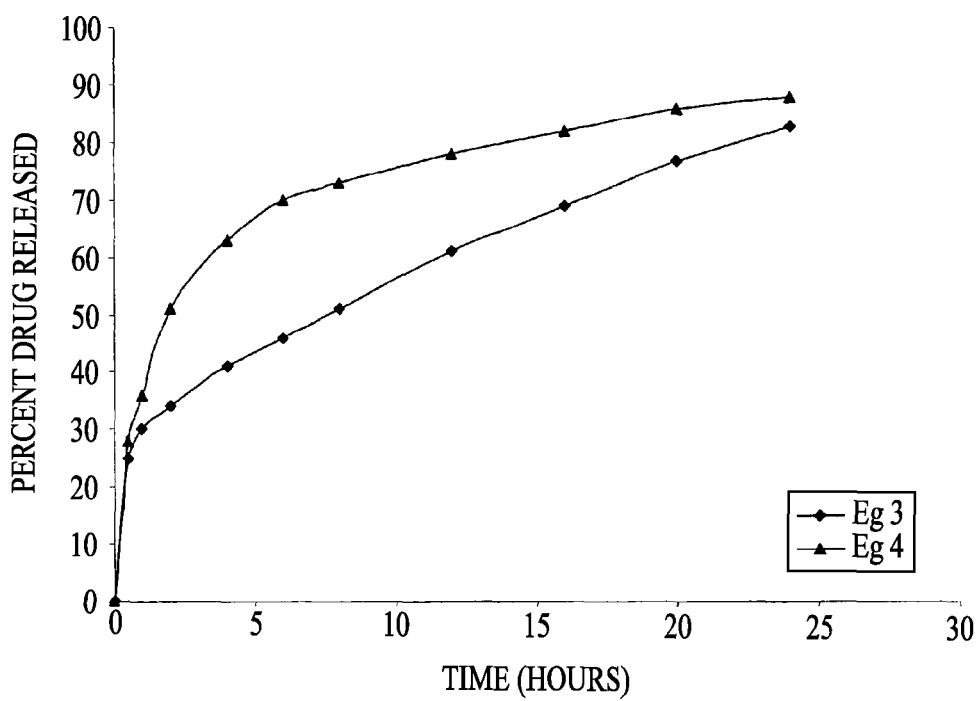

FIG. 5 is a graph showing percent drug (oxybutynin) released versus time from formulations of Examples 3 and 4.

Any of the embodiments illustrated herein are provided for the purpose of illustration only and are by no means meant to narrow the scope of the present invention.

DETAILED DESCRIPTION OF THE INVENTION

The present invention provides an oral drug delivery system comprising—

(a) a core comprising an active ingredient composition comprising at least one active ingredient and a pharmaceutically acceptable excipient, and (b) a coating surrounding the core, wherein the drug delivery system is designed in a manner such that the coating is reliably removed fully or partially from one or more preselected surfaces of the system upon contact with an aqueous environment, provided further that the coating is not removed from at least one of the surfaces.

Accordingly, the coating is partially removed from the system but may be fully or partially removed from one or more preselected surfaces. Hereafter, unless it is specified that the coating is removed from a surface the use of the term 'partial removal of coating' will refer to partial removal from the system.

The term "reliably" as used herein means that the coating is removed from the preselected surfaces and does not rupture from any other non-selected weak point in the coating. In contrast, the prior art system of PCT publication no. WO 02/080887 teaches a system where the opening of the system occurs reliably in time i.e. at a predetermined time but the surface that would rupture is unpredictable; in the present invention the term "reliably" refers to the removal of coating from any one or more of a preselected surface. Further in contrast, prior art system disclosed in U.S. Pat. Nos. 6,720, 005 and 6,733,784 rupture "mostly" around the belly-band area only and do not allow pre-selection of any other surface.

More particularly, the present invention provides an oral drug delivery system comprising—

(a) a core comprising an active ingredient composition comprising at least one active ingredient and a pharmaceutically acceptable excipient, and (b) a coating surrounding the core, wherein the oral drug delivery system is in the form of a coated tablet and includes a feature such that the coating is removed partially or fully from one or more of the tablet surfaces upon contact with an aqueous environment, further wherein the feature is such that it enables the selection of any of the tablet surface or surfaces from which the coating is desired to be partially or fully removed, provided further that the coating is not removed from at least one of the surfaces.

The oral drug delivery system of the present invention is designed such that the coating is removed fully or partially from a preselected surface or surfaces upon contact with an aqueous environment and not removed from at least one of the surfaces. The partial removal of the coating may be affected by several means and the features enabling the same may be features of the coating or the core, or both, operating cooperatively. For example, the system may be designed such that the coating is soluble or dissolved from one surface of the system, but not dissolved from the other surfaces of the system, thus becoming partially removed from the system. Alternatively, the oral drug delivery system may be designed such that the coating is ruptured and removed fully or partially from one or more preselected surfaces of the system upon contact with an aqueous environment. As used herein the term "defective coating" refers to coatings that are susceptible to rupture due to a weakness. The defective coating on the preselected surface may be made by creating a weakness in the coating by mechanical, chemical or electrical means, or by radiation, or by designing a brittle coating, or a thin coating, or a brittle and thin coating or a porous coating on the preselected surface or surfaces.

The defect may also be instantly created on the preselected surface by leaching of components of the coating upon contact with the aqueous environment. The leachable components may be selected by a person of skill in the art from known water soluble substances and suitable amounts ordinarily determined by routine optimization. Accordingly in one preferred embodiment of the present invention, the coating comprises one or more water insoluble polymers, leachable components and other conventional coating additives such as plasticizers, colour and mixtures thereof and the like.

Examples of leachable components that may be used include water soluble inorganic compounds and water soluble organic compounds. More specifically inorganic leachable compounds include, for example, sodium chloride, sodium bromide, sodium carbonate, potassium chloride, potassium sulfate, potassium phosphate, potassium nitrate, calcium phosphate, calcium nitrate, calcium chloride, and the like. More specifically, leachable organic compounds include, water soluble polymers such as water soluble cellulose polymers, polyols, for example polyhydric alcohol, polyalkylene glycol, polyglycol and the like. Organic compounds that may be used as leachable components also includes glucose, sucrose, sorbitol, mannitol, lactitol, lactose, sodium benzoate, sodium acetate, sodium citrate and the like.

The defect may also be in the form of an apparent fault such as an indent or a tear or a cut or an etching, which beginning from the outer surface of the coating may penetrate only partially through the coating or may penetrate completely to the inner surface of the coating so as to form a passageway.

In other words, a skilled artisan would understand that no limitation should be read in the coating, and that the present invention includes cases where the coating may be defective or without any defect or a combination.

The core may be designed with a swellable or a reactive composition in the vicinity of the preselected surface. In preferred embodiments of the present invention, the core is swellable, and the coating is impermeable to the active ingredient and has a passageway therein. Upon contact with an aqueous environment, water permeates through the passageway, the core swells and the coating ruptures from the selected surface or surfaces that have one or more passageways. The reactive composition is reactive with the coating in that in the presence of ingredients released from the reactive composition, the coat in the vicinity dissolves, disintegrates or is weakened. For example a reactive composition comprising ethanol microencapsulated with a water soluble coat will release ethanol on imbibing of water into the core by the system and the ethanol in turn will dissolve ethylcellulose containing not less than 46.5% of ethoxy groups present as component of the coating thereby weakening and removing the coating.

The coating surrounding the core of the oral drug delivery system of the present invention is preferably impermeable to the active ingredient, and has a passageway therein. In one preferred embodiment of the coating with a passageway, the coating is made up of water-insoluble polymers that may be selected from ethyl cellulose, hydrophobic methacrylic acid derivatives and the like, and mixtures thereof. Preselected one or more surfaces of the coating are then provided with a mechanically or laser-drilled passageway, and cause the core to partially remove the coating, thereby exposing a portion of the core for the release of the active ingredient contained therein. In more preferred embodiments of the present invention wherein the coating has a passageway, the oral drug delivery system is in the form of a tablet. The passageways in the coating may be provided on one or more preselected surfaces of the tablet, such that when water from the surrounding environment enters the tablet through the passageway, the core causes partial removal of the coating from the preselected surfaces, thereby exposing a defined surface area for release of the active ingredient. In preferred embodiments the core has components that are swellable or reactive to the coating.

Embodiments of the present invention provide an oral drug delivery system comprising—
  a. a core comprising an active ingredient composition comprising at least one active ingredient and pharmaceutically acceptable excipients, and
  b. a coating surrounding the core,
wherein the oral drug delivery system has at least two surfaces and is designed in a manner such that the coating is removed fully or partially from one of the surfaces when the oral drug delivery system contacts an aqueous environment and further wherein the coating is removed from the surface different from the one having the least surface area. The oral drug delivery systems of the present invention provide benefit over prior art systems which do not provide a flexibility in choice of the surface from which the coating can be removed, and generally expose the surface with the lower surface area.

Specific embodiments of the present invention also provide aforesaid oral drug delivery system, which release the drug without a substantial delay after the oral drug delivery system contacts an aqueous environment. The term "without a substantial delay" as used herein means that the active ingredient release is initiated from the controlled drug delivery system of the present invention within 0 to 60 minutes from the time the core contacts an aqueous environment, preferably within 0 to 20 minutes, and most preferably within 0 to 5 minutes.

In one embodiment of the present invention, the active ingredient composition is a swellable composition comprising at least one active ingredient and a swelling agent. In another embodiment of the present invention, the core comprises active ingredient composition and swellable composition, which may be present as one or more layers. The active ingredient present in these layers may be the same or different.

In one embodiment of the present invention the active ingredient is isolated from its environment by providing an oral drug delivery system comprising— a. a core comprising the active ingredient and pharmaceutically acceptable excipients, and b. a coating surrounding the core, wherein the system has a feature such that upon contact with an aqueous environment the coating ruptures to provide instant and rapid release of the active ingredient. Such systems are useful for active ingredients that are bitter in taste, or active ingredients that irritate the mucosal surface. Also, the system is useful for active ingredients that need to be protected from being degraded by contact with fluids from the surrounding environment.

The partial removal of the coating may also be affected by including a composition comprising gas generating agents in the core, such that when the coating contacts an aqueous environment, the gas generating agents release gas, generating pressure that causes the coating to be removed partially. Preferably, the swellable composition may comprise a mixture of swellable excipients and gas generating agents, the mixture being designed with types and amounts of components selected so as to cause the removal of the coating and initiation of release without a substantial delay or to cause a predetermined period of delay.

The swellable composition used in oral drug delivery system of the present invention comprises a swellable agent that may be selected from a group comprising a swellable excipient, a gas generating agent and mixtures thereof. The swelling agent is generally used in an amount ranging from about 0.5% to about 95% by weight of the swellable composition. The swellable excipient that may be used may be a highly swellable excipient selected from vinylpyrrolidone polymers such as crospovidone; cellulose and cellulose derivatives such as carboxyalkyl celluloses, crosslinked carboxyalkylcelluloses and their alkali salts; sodium starch glycolate, starch and starch derivatives, resins and mixtures thereof. The highly swellable excipient is preferably used in an amount ranging from about 2% to about 35% by weight of the swellable composition. The swellable excipient that may be used may be a moderately swellable excipient and may be used in an amount ranging from about 5% to about 70% by weight of the swellable composition, preferably about 50% to about 70% by weight of the swellable composition. Gas generating agents that may be used in the present invention include carbonates such as calcium carbonate, bicarbonates such as sodium or potassium bicarbonate, sulfites such as sodium sulfite, sodium bisulfite, or sodium metabisulfite, and the like. These salts may be used alone or in combination with an acid source as a gas generating couple. The acid source may be an edible organic acid, a salt of an edible organic acid, acidic components such as acrylate polymers, or mixtures thereof. Examples of organic acids that may be used include citric acid, malic acid, succinic acid, tartaric acid, fumaric acid, maleic acid, ascorbic acid, glutamic acid, and their salts, and mixtures thereof.

The swellable composition may further comprise a wicking agent in an amount ranging from about 0.5% to about 10% by weight of the swellable composition. Examples of wicking agents that may be used include, but are not limited to, colloidal silicon dioxide, kaolin, titanium dioxide, fumed silicon dioxide, alumina, niacinamide, sodium lauryl sulfate, low molecular weight polyvinylpyrrolidone, m-pyrol, bentonite, magnesium aluminum silicate, polyester, polyethylene. Preferably, the wicking agents used in the pharmaceutical composition of the present invention include cellulose and cellulose derivatives, colloidal silicon dioxide, and mixtures thereof.

The swellable composition may also comprise osmogents in an amount ranging from about 0.5% to about 10% by weight of the swellable composition. Examples of osmogents that may be used include, but are not limited to, inorganic salts such as magnesium chloride or magnesium sulfate, lithium, sodium or potassium chloride, lithium, sodium or potassium hydrogen phosphate, lithium, sodium or potassium dihydrogen phosphate, salts of organic acids such as sodium or potassium acetate, magnesium succinate, sodium benzoate, sodium citrate or sodium ascorbate; carbohydrates such as mannitol, sorbitol, arabinose, ribose, xylose, glucose, fructose, mannose, galactose, sucrose, maltose, lactose, raffinose; water-soluble amino acids such as glycine, leucine, alanine, or methionine; urea and the like; osmopolymers selected from the group consisting of poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly crosslinked with glyoxal, formaldehyde, glutaraldehyde and having a degree of polymerization from 2,000 to 30,000; poly(ethylene oxide) having a molecular weight from 10,000 to 7,8000,000; acidic carboxy polymers known as carboxypolymethylene or as carboxyvinyl polymers, a polymer consisting of acrylic acid lightly cross-linked with polyallylsucrose and sold under the trademark Carbopol®, acidic carboxy polymer having a molecular weight of 200,000 to 6,000,000, including sodium acidic carboxyvinyl hydrogel and potassium acidic carboxyvinyl hydrogel; Cyanamer® polyacrylamide; and the like, and mixtures thereof.

In one embodiment of the present invention, the coating surrounding the core is semipermeable in nature and may be obtained by using water-insoluble agents like cellulose derivatives such as cellulose acetate, ethyl cellulose and the like, in admixture with a sufficient amount of one or more water-soluble polymers selected from methyl cellulose, hydroxypropyl methylcellulose, hydroxyethyl cellulose, hydroxypropyl cellulose, polyvinylpyrrolidone and mixtures thereof, such that the properties of the semipermeable coating are modified, thereby allowing the coating to be removed partially upon contact with an aqueous environment. The coating does not have any passageway therein. The term "semipermeable" as used herein to describe a coating refers to a coating which is permeable to water or ions but not permeable to an active ingredient. The coating being semipermeable in nature allows water from the surrounding environment to enter the system, thereby causing the core to remove the coating partially so as to expose a defined surface area for release of the active ingredient. In a preferred embodiment of the present invention, a mixture of a water-soluble polymer and a water-insoluble polymer is used to obtain the coating. For example, a mixture of ethyl cellulose and hydroxypropyl methylcellulose, or a mixture of ethyl cellulose and polyvinylpyrrolidone, may be used to obtain the coating. In embodiments where the coating does not have a passageway, the oral drug delivery system may be coated to a weight gain in the range of about 2% to about 6.5% by weight of the core, such that the active ingredient is released without a substantial delay or may be coated to higher percentage for designing a programmed delay of release into the system. When release without a substantial delay is desired it is preferable that the coating have a passageway. In these embodiments, the release without a substantial delay is obtained more easily and a wide range of coating weights may be used.

The water soluble polymer in the semi permeable coating of this embodiment may alternatively be replaced by other leachable components or alternatively a mixture of water soluble polymer and other leachable components may be present.

The dry weight ratio of the water insoluble polymer to the leachable component ranges from about 10:90 to about 90:10; more preferably from about 60:40 to about 40:60 and most preferably from about 70:30 to about 95:5. Examples of water insoluble polymers are known to a person of skill in the art and are available commercially. For example, water insoluble polymers that may be used include, but are not limited to, ethyl cellulose, cellulose acetate, polyvinyl acetate, nitrocellulose, butadiene styrene copolymers, and water insoluble methacrylate copolymers. Preferably, the water insoluble polymer is selected from the group consisting of ethyl cellulose, poly(ethyl acrylate, methyl methacrylate, triethylammonioethyl methacrylate chloride) such as, for example, those commercially available under the trade names Eudragit RS100, Eudragit RS PO, Eudragit RS 30D and Eudragit RS 12.5 and poly (ethyl acrylate, methyl methacrylate, trimethylammonioethymethacrylate chloride such as those commercially available under the trade names Eudragit RL100, Eudragit RL PO, Eudragit RL 30D and Eudragit RL 12.5. Examples of water insoluble polymers that are insoluble below a pH of about 4.0 but soluble at pH above 7.0 include poly(methacrylic acid, methyl methacrylate such as for example, those commercially available under the tradenames Eudragit L 100, Eudragit L 12.5, Eudragit 12.5 P), Poly (methacrylic acid, ethyl acrylate) such as those commercially available under the trade names Eudragit L 30 D-55, Eudragit L 100-55, Eastacryl 30 D, Kollicoat MAE 30 D and Kollicoat MAE 30 DP) and poly(methacrylic acid, methyl methacrylate) such as those commercially available under the trade names Eudragit S 100, Eudragit S 12.5, Eudragit S 12.5 P), cellulose acetate phthalate, hydroxypropyl methyl cellulose acetate succinate and the like and mixture thereof.

According to this embodiment of the present invention with a leachable component in the coating, the coating is applied to the core of the tablet to a weight gain of about 5% to about 20% by weight of the core, preferably from about 8% to about 18% by weight of the core tablet.

According to the present invention, the coating comprises one or more plasticizers. The plasticizers may be those that are conventionally used in the pharmaceutical art. These may be hydrophilic or hydrophobic in nature. Examples of hydrophilic plasticizer that may be used in the coating, include, but are not limited to, triethyl citrate, triethyl acetyl citrate, triacetin, tributyl citrate, polyethylene glycol 6000, polysorbate 80, glycerol and the like and mixtures thereof. Examples of hydrophobic plasticizer that may be used in the coating include, but are not limited to, dibutyl sebacate, diethyl sebacate, diethyl phthalate, vegetable and mineral oil, glyceryl tributyrate and the like and mixtures thereof. More preferably, the plasticizer is a mixture of hydrophobic and hydrophilic plasticizers. In a particular embodiment wherein the coating comprises ethyl cellulose as the water insoluble polymer, the hydrophobic plasticizer is dibutyl sebacate and the hydrophilic plasticizer is triethyl citrate, preferably in the ratio of about 5:1. More particularly, the percent of dibutyl sebacate by weight of ethyl cellulose is about 5% and the percent of triethyl citrate is about 25% by weight of ethyl cellulose.

According to this embodiment of the present invention with a leachable component in the coating, upon contact with the aqueous environment, the leachable component(s) in the coating of the oral drug delivery system dissolves to form a micro porous coating. Water permeates through the coating and interacts with the swellable or reactive composition. Upon imbibing water, the swellable composition or the reactive composition swells or reacts causing the coating on the surface in it's immediate vicinity to be removed. The active ingredient composition layer is exposed to the aqueous environment. A control on the release of the active ingredient may be obtained by designing into the system an exposure to aqueous environment by removal of the coating from only a very limited surface area. The coating is removed only from the preselected surface or surfaces without a substantial delay.

In one embodiment of the present invention, the core comprises an active ingredient composition comprising at least one active ingredient and pharmaceutically acceptable excipients. In another embodiment of the present invention, the active ingredient composition is a swellable composition comprising at least one active ingredient, and a swelling agent. In yet another embodiment of the present invention, the core comprises an active ingredient composition and swellable composition, which may both be present as one or more layers. The active ingredient present in these layers may be the same or different. Each of these embodiments comprises a coating surrounding the core, which is semipermeable in nature, and does not have any passageway.

The oral drug delivery system of the present invention may be designed to release the active ingredient contained therein in a controlled manner, or it may be designed to provide instant and rapid release of the active ingredient similar to uncoated conventional dosage forms while providing the desirable protection of the coating. Accordingly, the core of the oral drug delivery system comprises pharmaceutically acceptable excipients that govern the rate of release of the active ingredient from the core. The pharmaceutical excipients are selected so as to provide a conventional release, or controlled release, preferably zero-order release of the active ingredient.

In one embodiment of the present invention, the oral drug delivery system is designed to release the active ingredient in a controlled manner. The active ingredient composition therefore comprises rate controlling excipients that may be selected from hydrophilic polymers such as methyl cellulose, hydroxypropyl methylcellulose, hydroxyethyl cellulose, hydroxypropyl cellulose, hydroxyethyl methylcellulose, carboxymethylcellulose and sodium carboxymethylcellulose; hydrophobic compounds such as ethyl cellulose, glycerol palmitostearate, beeswax, glycowax, castor wax, carnauba wax, glycerol monostearate, stearyl alcohol, glycerol behenic acid ester, cetyl alcohol, natural and synthetic glycerides, waxes, fatty acids, hydrophobic polyacrylamide derivatives, hydrophobic methacrylic acid derivatives; vinyl pyrrolidone polymers such as polyvinylpyrrolidone and copolymers of vinyl pyrrolidone and vinyl acetate; alkylene oxide homopolymers; gums of plant, animal, mineral or synthetic origin; and mixtures thereof. The active ingredient composition may comprise one or more of the rate controlling excipients mentioned above in an amount ranging from about 2% to about 90% by weight of the core; the specific amounts and type may be selected to either not cause a substantial delay in the initiation of release or to provide a programmed delay in the initiation of release.

The active ingredient composition used in the core of the controlled drug delivery system of the present invention comprises one or more active ingredient, rate controlling excipients and other pharmaceutically acceptable excipients. Drugs that may be used in the pharmaceutical composition of the present invention may be selected from the following, viz. alcohol abuse preparations, drugs used for Alzheimer's disease, anesthetics, acromegaly agents, analgesics, antiasthmatics, anticancer agents, anticoagulants and antithrombotic agents, anticonvulsants, antidiabetics antiemetics, antiglaucoma, antihistamines, anti-infective agents, antiparkinsons, antiplatelet agents, antirheumatic agents, antispasmodics and anticholinergic agents, antitussives, carbonic anhydrase inhibitors, cardiovascular agents, cholinesterase inhibitors, treatment of CNS disorders, CNS stimulants, contraceptives, cystic fibrosis management, dopamine receptor agonists, endometriosis management, erectile dysfunction therapy, fertility agents, gastrointestinal agents, immunomodulators and immunosuppressives, memory enhancers, migraine preparations, muscle relaxants, nucleoside analogues, osteoporosis management, parasympathomimetics, prostaglandins, psychotherapeutic agents, sedatives, hypnotics and tranquilizers, drugs used for skin ailments, steroids and hormones.

In one embodiment of the present invention, the core comprises—
a. a first layer of active ingredient composition
b. a second layer of active ingredient composition, and
c. a third layer of a swellable composition,
wherein the active ingredient compositions of the first and second layer may comprise active ingredients that are same or different, and the swellable composition comprises a swelling agent, and may or may not comprise an active ingredient.

In one embodiment of the present invention, the swellable composition is present as an in-lay tablet in a core comprising the active ingredient composition. The term "in-lay tablet" is well known in the art, see for example, Lieberman H. A. et. al., "Pharmaceutical Dosage Forms: Tablets, Volume 1, Second Edition revised and expanded, Marcel Dekker, Page 273, 1989. The core with the in-lay tablet is coated with an impermeable coating having a passageway on the surface immediately above the swellable composition. The swellable composition ruptures the coat upon contact with aqueous environment, thereby exposing a defined surface area. The active ingredient is then released from the exposed surface.

In another embodiment of the present invention, the core is compressed into a bilayer tablet; the first layer comprising the active ingredient composition having uninterrupted plain surfaces surrounded by coating or the second layer; and the second layer comprising the swellable composition having at least one surface interrupted by at least one depression or cavity. The coating used in this embodiment is semipermeable in nature and the water entering the system causes the coating to be removed from the surface having the depression or cavity.

In some embodiments of the present invention, any of the aforesaid oral drug delivery systems may be further coated with an outer pH-dependent coating that partially or completely covers the inner coating, which immediately surrounds the core. An intermediate seal coating may be provided between the inner coating and the outer pH-dependent coating. pH-dependent polymers commonly used in the art may be used to provide the outer coating.

The examples that follow do not limit the scope of the invention and are merely used as illustrations.

EXAMPLE 1

Oral drug delivery systems comprising metoprolol succinate were obtained as per the present invention, as detailed in Table 1 below.

TABLE 1

| Ingredients | Quantity (mg/tablet) | | | |
|---|---|---|---|---|
| | I | II | III | IV |
| First layer | | | | |
| Metoprolol succinate | 35.625 | 47.5 | 47.5 | 47.5 |
| Hydroxypropyl methylcellulose (HPMC K15M) | 15.0 | 20.0 | — | — |
| Hydroxypropyl methylcellulose (HPMC K100M) | — | — | 20.0 | — |
| Polyvinylpyrrolidone (PVP K30) | 7.5 | 10.0 | 10.0 | 10.4 |
| Lactitol monohydrate | 15.0 | 20.0 | 20.0 | — |
| Microcrystalline cellulose | — | — | — | 44.5 |
| Hydroxypropyl methylcellulose (HPMC E50LV) | — | — | — | 10.0 |
| Sodium starch glycolate | 15.0 | 20.0 | 20.0 | — |
| Colloidal silicon dioxide | 0.375 | 0.5 | 0.5 | 1.2 |
| Talc | 1.125 | 1.5 | 1.5 | 1.7 |
| Magnesium stearate | 1.125 | 1.5 | 1.5 | 1.7 |
| Aquacoat ECD 30 (solids) | — | — | — | 18.0 |
| Second layer | | | | |
| Metoprolol succinate | 11.875 | — | — | — |
| Silicified microcrystalline cellulose (Prosolv SMCC 90) | 20.0 | 34.32 | 34.32 | 34.32 |
| Crospovidone | — | 12.18 | 12.18 | 12.18 |
| Colloidal silicon dioxide | 0.75 | 1.22 | 1.22 | 1.22 |
| Sodium bicarbonate | 4.0 | — | — | — |
| Eudragit L-100-55 | 12.0 | — | — | — |
| Mannitol SD 200 | 20.0 | — | — | — |
| Sodium lauryl sulfate | 0.375 | 0.48 | 0.48 | 0.48 |
| Magnesium stearate | 2.0 | 0.5 | 0.5 | 0.5 |
| Talc | 2.0 | 0.12 | 0.12 | 0.12 |
| Colour | q.s. | q.s. | q.s. | q.s. |
| Coating | | | | |
| Ethyl cellulose (as aqueous dispersion Aquacoat ® ECD 30) Dibutyl sebacate Triethyl citrate | Coated to a weight gain of 8% by weight of the core | Coated to a weight gain of 15% by weight of the core | Coated to a weight gain of 15% by weight of the core | Coated to a weight gain of 15% by weight of the core |

The oral drug delivery systems of Formulae I, II, III and IV were made as follows. Metoprolol succinate, HPMC, lactitol monohydrate and povidone K-30 were passed through ASTM (American Society for Testing and Materials) sieve # 40 and mixed suitably. The mixture thus obtained was granulated with purified water to a suitable end-point, and the granules obtained were dried to a moisture content of about 1-2%. The dried granules were milled suitably and lubricated with a mixture of sodium starch glycolate, colloidal silicon dioxide, talc and magnesium stearate, to obtain the blend for the first layer.

Silicified microcrystalline cellulose, crospovidone, sodium lauryl sulfate and a suitable colour were passed through ASTM sieve #40 and mixed suitably. The blend so obtained was lubricated with a mixture of colloidal silicon dioxide and magnesium stearate (previously passed through ASTM sieve #60). In case of the system of Formula I, the blend also included metoprolol succinate, Eudragit L-100-55, sodium bicarbonate and Mannitol in amounts mentioned above.

The above two preparations were compressed to obtain bilayer tablets, which were coated with an aqueous dispersion of ethyl cellulose to a suitable weight gain. An orifice was then drilled on one side of the tablet.

The tablets thus obtained were subjected to dissolution testing. Tablets of Formula I were tested using United States Pharmacopoeia dissolution apparatus, type II, using 500 ml of 0.01N HCl as the dissolution medium, at 100 rpm. Tablets of Formulae II, III and IV were tested using United States Pharmacopoeia dissolution apparatus, type II, using 500 ml of pH 6.8 buffer as the dissolution medium, at 50 rpm. The results of the dissolution test are recorded in Table 2 below.

TABLE 2

| Time (hours) | Percent drug released | | | |
| --- | --- | --- | --- | --- |
| | Formula I | Formula II | Formula III | Formula IV |
| 0.25 | 18 | — | — | — |
| 0.5 | 21 | — | — | — |
| 1.0 | 24 | 6 | 5 | 8 |
| 2.0 | 31 | 12 | 11 | 13 |
| 4.0 | 51 | 24 | 21 | 23 |
| 8.0 | 84 | 46 | 39 | 37 |
| 12.0 | 96 | 64 | 55 | 49 |
| 16.0 | — | 84 | 71 | 58 |
| 20.0 | — | 99 | 85 | 67 |

The release from the controlled release layer of all the four systems was zero-order, i.e. linear over time (regression co-efficient r2 being 0.9697, 0.9959, 0.9966 and 0.9816 for Formula I, II III and IV, respectively).

EXAMPLE 2

A controlled release pharmaceutical composition of bupropion hydrochloride was obtained as per the present invention, as detailed in Table 3 below.

TABLE 3

| Ingredients | Quantity (mg/tab) | Percent by weight |
| --- | --- | --- |
| First Layer | | |
| Bupropion hydrochloride | 150.0 | 37.5 |
| Hydroxypropyl methylcellulose (HPMC K100M Premium) | 20.00 | 5.0 |
| Lactose anhydrous (DCL 21) | 177.0 | 44.25 |
| Polyvinylpyrrolidone (PVP K-30) | 13.0 | 3.25 |
| Colloidal silicon dioxide | 4.0 | 1.00 |
| Stearic acid | 12.0 | 3.00 |
| Talc | 4.00 | 1.00 |
| Sodium starch glycolate | 20.00 | 5.0 |
| Second layer | | |
| Silicified microcrystalline cellulose (Prosolv SMCC 90) | 205.0 | 70.7 |
| Crospovidone | 72.5 | 25.0 |
| Colloidal silicon dioxide | 7.2 | 2.5 |
| Sodium lauryl sulfate | 2.90 | 1.0 |
| Magnesium stearate | 2.4 | 0.83 |
| Colour | q.s. | |
| Coating | | |
| Ethyl cellulose (as aqueous dispersion Aquacoat ®) | Coated to 14% by weight of the core tablet | |
| Dibutyl sebacate | | |

Bupropion hydrochloride, HPMC K100M lactose anhydrous, PVP K-30 and colloidal silicon dioxide were passed through ASTM sieve #40 and mixed thoroughly. Stearic acid and talc were passed through ASTM sieve # 60 and mixed with the blend, to obtain the composition of the first layer.

Prosolv SMCC 90, colloidal silicon dioxide, sodium lauryl sulfate, crospovidone and colour were passed through ASTM sieve # 40 and mixed thoroughly to obtain a blend. This blend was lubricated with magnesium stearate, to obtain the composition of the second layer.

The two compositions were compressed using standard concave punches to obtain bilayer tablets. The compressed tablets were coated with the coating composition to a weight gain of about 14% by weight of the core. An orifice was drilled on the side of the tablet that contained the second layer, i.e. the layer without bupropion hydrochloride.

The tablets thus obtained were subjected to dissolution testing using United States Pharmacopoeia dissolution apparatus, type II, using 900 ml of water as the dissolution medium, at 50 rpm. The results of the dissolution test are tabulated in Table 4 below. The release was zero-order, i.e. linear over time (regression co-efficient r=0.97).

TABLE 4

| Time (hours) | % drug released |
| --- | --- |
| 1 | 6 |
| 2 | 13 |
| 3 | 18 |
| 4 | 22 |
| 6 | 31 |
| 8 | 37 |
| 10 | 43 |
| 12 | 49 |
| 16 | 56 |

TABLE 4-continued

| Time (hours) | % drug released |
|---|---|
| 20 | 67 |
| 24 | 74 |

EXAMPLE 3

A controlled release pharmaceutical composition of oxybutynin chloride was obtained as per the present invention, as detailed in Table 5 below.

TABLE 5

| Ingredients | Quantity (mg/tab) | Percent by weight |
|---|---|---|
| First Layer | | |
| Oxybutynin chloride | 3.75 | 5.36 |
| Silicified microcrystalline cellulose (Prosolv SMCC 90) | 46.64 | 66.62 |
| Colloidal silicon dioxide | 1.65 | 2.35 |
| Crospovidone | 16.56 | 23.65 |
| Sodium lauryl sulfate | 0.66 | 0.94 |
| Colour | 0.198 | 0.28 |
| Magnesium stearate | 0.53 | 0.76 |
| Second layer | | |
| Oxybutynin chloride | 7.50 | 6.0 |
| Hydroxypropyl methylcellulose (HPMC K4M) | 20.0 | 16.0 |
| Lactitol monohydrate | 40.0 | 32.0 |
| Citric acid, anhydrous | 2.50 | 2.0 |
| Microcrystalline cellulose (Avicel PH 102) | 33.0 | 26.4 |
| Sodium starch glycolate | 20.0 | 16.0 |
| Talc | 1.00 | 0.8 |
| Magnesium stearate | 1.00 | 0.8 |
| Coating | | |
| Ethyl cellulose (as aqueous dispersion Aquacoat ®) Dibutyl sebacate Triethyl citrate | Coated to about 14% by weight of the core tablet | |

The bilayered tablet was made as follows. Oxybutynin chloride was mixed with Prosolv SMCC 90, colloidal silicon dioxide, crospovidone, sodium lauryl sulfate, colour and magnesium stearate to obtain a first layer composition. The second layer composition was obtained by blending together a mixture of oxybutynin chloride, HPMC K4M, lactitol monohydrate and citric acid. The mixture was granulated using purified water and the granules so obtained were lubricated with a mixture of microcrystalline cellulose, sodium starch glycolate, talc and magnesium stearate. The first and second layer compositions were then compressed to obtain the bilayered tablets, which were then coated with a coating composition comprising aquacoat, dibutyl sebacate and triethyl citrate to a weight gain of about 14% by weight of the core tablet.

The tablets thus obtained were subjected to dissolution testing using United States Pharmacopoeia dissolution apparatus, type II, using 900 ml of pH 4.5 buffer as the dissolution medium, at 100 rpm. The results of the dissolution test are recorded in Table 6 below. The release from the controlled release layer was zero-order, i.e. linear over time (regression co-efficient $r^2=0.9904$).

TABLE 6

| Time (hours) | % drug released |
|---|---|
| 0.5 | 25 |
| 1 | 30 |
| 2 | 34 |
| 4 | 41 |
| 6 | 46 |
| 8 | 51 |
| 12 | 61 |
| 16 | 69 |
| 20 | 77 |
| 24 | 83 |

EXAMPLE 4

A trilayered oral drug delivery system comprising oxybutynin chloride was obtained as per Table 7 below.

TABLE 7

| Ingredients | Quantity (mg/tablet) | Percent by weight |
|---|---|---|
| First layer | | |
| Oxybutynin chloride | 3.75 | 5.36 |
| Silicified microcrystalline cellulose (Prosolv SMCC 90) | 46.64 | 66.62 |
| Colloidal silicon dioxide | 1.65 | 2.35 |
| Crospovidone | 16.56 | 23.65 |
| Sodium lauryl sulfate | 0.66 | 0.94 |
| Colour | 0.198 | 0.28 |
| Magnesium stearate | 0.53 | 0.76 |
| Second layer | | |
| Oxybutynin chloride | 7.50 | 6.0 |
| Hydroxypropyl methylcellulose (HPMC K4M) | 20.0 | 16.0 |
| Lactitol monohydrate | 40.0 | 32.0 |
| Citric acid, anhydrous | 2.50 | 2.0 |
| Microcrystalline cellulose (Avicel PH 102) | 33.0 | 26.4 |
| Sodium starch glycolate | 20.0 | 16.0 |
| Talc | 1.00 | 0.8 |
| Magnesium stearate | 1.0 | 0.8 |
| Third layer | | |
| Oxybutynin chloride | 3.75 | 5.36 |
| Silicified microcrystalline cellulose (Prosolv SMCC 90) | 46.64 | 66.62 |
| Colloidal silicon dioxide | 1.65 | 2.35 |
| Crospovidone | 16.56 | 23.65 |
| Sodium lauryl sulfate | 0.66 | 0.94 |
| Colour | 0.198 | 0.28 |
| Magnesium stearate | 0.53 | 0.76 |
| Coating | | |
| Ethyl cellulose (as aqueous dispersion Aquacoat ®) Dibutyl sebacate Triethyl citrate | Coated to about 14% by weight of the core tablet | |

The three layers were obtained as mentioned in examples above and compressed to obtain the core, which was then coated with the coating solution to a weight gain of about 14% by weight of the core. An orifice of size 400 microns was drilled on one planar surface of the tablet.

The trilayered tablets thus obtained were subjected to dissolution testing using United States Pharmacopoeia dissolution apparatus, type II, using 900 ml of pH 4.5 buffer as the dissolution medium, at a speed of 100 rpm. The results of the dissolution testing are recorded in Table 8 below.

TABLE 8

| Time (hours) | Percent drug released |
|---|---|
| 0.5 | 28 |
| 1 | 36 |
| 2 | 51 |
| 4 | 63 |
| 6 | 70 |
| 8 | 73 |
| 12 | 78 |
| 16 | 82 |
| 20 | 86 |
| 24 | 88 |

EXAMPLE 5-10

The ingredients of the active ingredient composition and the swellable composition are tabulated in Table 9. The bilayer core having active ingredient composition layer and the swellable composition layer was made according to the process as described in example 1.

TABLE 9

| Ingredients | mg per tablet | % by weight of the active ingredient composition |
|---|---|---|
| Active ingredient composition layer | | |
| Metoprolol Succinate | 11.875 | 20.47 |
| Hydroxypropyl methyl cellulose K100M | 20.0 | 34.48 |
| Hydroxypropyl methyl cellulose K4M | 7.0 | 12.06 |
| Lactose | 76.125 | 79.52 |
| Povidone | 10.0 | 17.24 |
| Methacrylic acid copolymer Type C | 10.0 | 17.24 |
| Colloidal Silicon Dioxide | 2.0 | 3.44 |
| Talc | 2.5 | 4.31 |
| Magnesium Stearate | 2.5 | 4.31 |
| Total | 58 mg | |

| Swellable composition layer | mg per tablet | % by weight of the swellable composition |
|---|---|---|
| Silicified microcrystalline cellulose | 46.4 | 32.67 |
| Colloidal Silicon Dioxide | 1.45 | 1.02 |
| Crospovidone | 8.7 | 6.126 |
| Sodium lauryl Sulphate | 0.58 | 0.40 |
| Red Oxide of Iron | 0.116 | 0.08 |
| Magnesium stearate | 0.609 | 0.428 |
| Talc | 0.145 | 0.102 |
| Total | 142 | |

The bilayer core prepared according to composition of table 9 was coated with the coating compositions tabulated in Table 10 to give coated tablets of examples 5-10. The coating compositions include leachable components such as mannitol, lactitol monohydrate, lactose, polyvinyl pyrrolidone, sodium lauryl sulphate, triethyl citrate and polysorbate 20.

TABLE 10

| Ingredients | Example 5 | Example 6 | Example 7 | Example 8 | Example 9 | Example 10 |
|---|---|---|---|---|---|---|
| | | | mg per tablet | | | |
| Bilayer core Coating composition | As in table 9 | As in table 9 | As in table 9 | As in table 9 | As in table 9 | As in table 9 |
| *Ethyl cellulose | 8.51 | 9.40 | 10.25 | 11.078 | 10.449 | 10.449 |
| *Cetyl alcohol | 0.3154 | 0.3487 | 0.3799 | 0.4103 | 0.348 | 0.348 |
| *Sodium lauryl Sulphate | 0.63 | 0.69 | 0.7532 | 0.8206 | 0.696 | 0.696 |
| mannitol | 3.04 | 1.88 | 0.91 | — | — | — |
| lactose | | | | — | 1.88 | — |
| Lactitol mohohydrate | — | — | — | — | — | 1.88 |
| Polyvinyl pyrrolidone | 0.61 | 0.47 | 0.23 | — | 0.47 | 0.47 |
| polysorbate 20 | 0.05 | 0.05 | 0.05 | — | 0.05 | 0.05 |
| Triethyl citrate | 0.47 | 0.52 | 0.57 | 0.62 | 0.52 | 0.52 |
| Dibutyl Sebacate | 2.37 | 2.62 | 2.85 | 3.08 | 2.62 | 2.62 |
| Ratio of Water insoluble:Water soluble | 63.8:36.2 | 74.52:25.5 | 80.31:19.69 | 94.69:5.3 | 74.39:25.60 | |
| % weight gain | | | 8% | | | |

TABLE 10-continued

| Ingredients | Example 5 | Example 6 | Example 7 | Example 8 | Example 9 | Example 10 |
|---|---|---|---|---|---|---|
| | | | mg per tablet | | | |
| Orifice Drilled | | no | | yes | no | |
| Opening time in dissolution bath (pH 6.8 buffer) in minutes | 3-6 | 5-6 | 60 | 1 | 12-27 | 4-8 |

*applied in the form of Aquacoat ECD 30 which is an aqueous dispersion containing ethyl cellulose (27% w/v), sodium lauryl sulphate 1% w/w and cetyl alcohol 2% w/v in water

EXAMPLE 11-13

The bilayer core comprising an active ingredient composition layer and the swellable composition layer having the ingredients as given in table 12, are prepared according to the process as described in example 1.

TABLE 12

| Ingredients | mg per tablet | % by weight of the active ingredient composition |
|---|---|---|
| Active ingredient layer | | |
| Venlafaxine hydrochloride | 169.710 | 34.77 |
| Hydroxypropyl methyl cellulose K4M | 36.00 | 7.37 |
| Polyvinyl pyrrolidone | 40.00 | 8.19 |
| Lactose monohydrate | 176.290 | 36.125 |
| Eudragit L100 55 | 60.0 | 12.2 |
| Talc | 3.0 | 0.61 |
| Magnesium stearate | 3.0 | 0.61 |

| Swellable composition layer | mg per tablet | % by weight of the swellable composition |
|---|---|---|
| Silicified microcrystalline cellulose | 113.116 | 79.65 |
| Colloidal Silicon Dioxide | 3.550 | 2.53 |
| Crospovidone | 21.300 | 15.0 |
| Sodium lauryl sulphate | 1.420 | 1.0 |
| FD & C Blue No. 1 Aluminum lake | 0.568 | 0.4 |
| Magnesium stearate | 1.491 | 1.05 |
| talc | 0.355 | 0.25 |

The bilayer core is then coated with the coating composition, details of which are given in table 13. The coating composition comprises a combination of leachable components such as sodium lauryl sulphate, triethyl citrate and polyvinyl pyrrolidone.

TABLE 13

| Ingredients | Example 11 | Example 12 | Example 13 |
|---|---|---|---|
| | | mg per tablet | |
| Bilayer core | As in table 12 | As in table 12 | As in table 12 |
| Coating composition | | | |
| *Ethyl cellulose | 23.03 | 20.81 | 23.03 |
| *Cetyl alcohol | 0.85 | 0.77 | 0.85 |
| *Sodium lauryl sulphate | 1.7 | 1.54 | 1.7 |
| Triethyl citrate | 1.28 | 1.16 | 1.28 |
| Dibutyl sebacate | 6.40 | 5.78 | 6.40 |
| Polyvinyl pyrrolidone | 5.76 | — | — |
| mannitol | — | 8.92 | — |
| Sucrose | — | — | 5.76 |
| Ratio of insoluble:soluble | 74.48:25.51 | 64.168:35.83 | 72.48:27.51 |
| % weight gain | 8 | 10 | 8 |

TABLE 13-continued

| Ingredients | Example 11 | Example 12 | Example 13 |
|---|---|---|---|
| | | mg per tablet | |
| Time of Opening of the tablet (in minutes) | 45-50 | 20 | 90 |

*applied in the form of Aquacoat ECD 30 which is an aqueous dispersion containing ethyl cellulose (27% w/v), sodium lauryl sulphate 1% w/w and cetyl alcohol 2% w/v in water

EXAMPLE 14

The active ingredient composition layer and the swellable composition layer having the ingredients given in table 14 were prepared by a process as described in the example 1. The bilayer core was then coated with a coating composition having ethyl cellulose as water insoluble polymer and leachable components which is a mixture of sodium lauryl sulphate, triethyl citrate, hydroxypropyl methyl cellulose low viscosity, polyethylene glycol 400 and polyethylene glycol 8000.

TABLE 14

| Ingredients | mgs per tablet | % by weight of active ingredient composition |
|---|---|---|
| Active ingredient composition layer | | |
| Metoprolol Succinate | 47.50 | 32.53 |
| Hydroxypropyl methyl cellulose K100M | 20.0 | 13.69 |
| Lactose directly compressible | 40.50 | 27.73 |
| Polyvinyl pyrrolidone | 10.0 | 6.85 |
| Eudragit L-100 55 | 10.0 | 6.85 |
| Hydroxypropyl methyl cellulose K4M | 15.0 | 10.27 |
| Aerosil | 0.50 | 0.34 |
| Talc | 1.25 | 0.85 |
| magnesium Stearate | 1.25 | 0.85 |

| Swellable composition layer | mgs per tablet | % by weight of swellable composition |
|---|---|---|
| Silicified microcrystalline Cellulose | 63.042 | 79.80 |
| Colloidal Silicon Dioxide | 1.975 | 2.50 |
| Crospovidone | 11.85 | 15.00 |
| Sodium Lauryl Sulphate | 0.79 | 1.00 |
| FD&C Blue No. 1 Alu Lake | 0.316 | 0.40 |
| Magnesium Stearate | 0.9875 | 1.25 |
| Talc | 0.1975 | 0.25 |

| Coating composition | mg per tablet |
|---|---|
| *Ethyl cellulose | 10.12 |
| *Cetyl alcohol | 0.37 |
| *Sodium lauryl sulphate | 0.74 |
| Triethyl citrate | 0.56 |
| Dibutyl sebacate | 2.81 |
| Hydroxypropyl methyl cellulose (6 cps) | 3.07 |
| Polyethylene glycol 400 | 0.153 |

TABLE 14-continued

| Polyethylene glycol 8000 | 0.153 |
| % weight gain | 8 |
| Ratio of insoluble:soluble | 68.39:31.60 |
| Time of Opening of the tablet (in mins) | 13-25 |

*applied in the form of Aquacoat ECD 30 which is an aqueous dispersion containing ethyl cellulose (27% w/v), sodium lauryl sulphate 1% w/w and cetyl alcohol 2% w/v in water While the invention has been described by reference to specific embodiments, this was done for purposes of illustration only and should not be construed to limit the spirit or the scope of the invention.

We claim:

1. A coated tablet comprising:
   a) a core comprising a first layer comprising active ingredient and a rate controlling excipient and a second layer comprising a swellable composition;
   b) a water insoluble coating surrounding the core, the coating comprising one or more water insoluble polymers and one or more water leachable components;
   wherein the water insoluble coating allows permeation of water after contact with an aqueous environment causing the second layer to swell and exert pressure on the coating, thereby removing only the coating that is in the immediate vicinity of the swellable composition but not the remaining portion, thereby exposing a defined surface area for release of the active ingredient for controlled release of active ingredient.

2. The coated tablet of claim 1, wherein the water insoluble coating is impermeable to the active ingredient.

3. The coated tablet of claim 1, wherein the swellable composition comprises a swelling agent.

4. The coated tablet of claim 3, wherein the swelling agent is selected from a swellable excipient, a gas generating agent and mixtures thereof.

5. The coated tablet of claim 1, wherein the swellable composition comprises wicking agents.

6. The coated tablet of claim 1, wherein the swellable composition comprises osmogents.

7. The coated tablet of claim 1, wherein the active ingredient is released without a substantial delay after the tablet contacts an aqueous environment.

8. The coated tablet of claim 1 further comprising an outer coating comprising a pH-dependent polymer.

9. The coated tablet of claim 1, wherein the swellable composition is in the form of an in-lay.

10. The coated tablet of claim 1, wherein the ratio of water insoluble polymer to leachable component varies from about 70:30 to about 95:5.

11. The coated tablet of claim 10, wherein the leachable component is selected from the group consisting essentially of: inorganic water soluble compounds, organic water soluble compounds and mixtures thereof.

12. The coated tablet of claim 1, wherein the water insoluble polymer in the coating is ethyl cellulose.

13. The coated tablet of claim 12, wherein the water insoluble coating further comprises a mixture of hydrophobic and hydrophilic plasticizers.

14. The coated tablet of claim 13, wherein the hydrophobic plasticizer is selected from the group consisting of dibutyl sebacate, diethyl sebacate, diethyl phthalate, vegetable and mineral oils and mixtures thereof.

15. The coated tablet of claim 14, wherein the ratio of dibutyl sebacate to triethyl citrate is about 5:1.

16. The coated tablet of claim 13, wherein the hydrophilic plasticizer is selected from the group consisting of triethyl citrate, triethyl acetyl citrate, triacetin, tributyl citrate, polyethylene glycol, glycerol and mixtures thereof.

* * * * *

UNITED STATES PATENT AND TRADEMARK OFFICE
CERTIFICATE OF CORRECTION

PATENT NO. : 8,470,367 B2  
APPLICATION NO. : 11/946575  
DATED : June 25, 2013  
INVENTOR(S) : Bhalachandra Dharmadhikari et al.

Page 1 of 1

It is certified that error appears in the above-identified patent and that said Letters Patent is hereby corrected as shown below:

In the Claims

In column 24, line 16, in Claim 11, after "consisting", delete "essentially", therefor Signed and Sealed this  
Twentieth Day of May, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,470,367 B2
APPLICATION NO. : 11/946575
DATED : June 25, 2013
INVENTOR(S) : Nitin Bhalachandra Dharmadhikari, Yashoraj Rupsinh Zala and Amarjit Singh It is certified that error appears in the above-identified patent and that said Letters Patent is hereby corrected as shown below:

In the Specification

Please replace the paragraph at Line 3 to Line 8 of Column 1 with the following paragraph:
--CLAIM OF PRIORITY
This application is a continuation in part of U.S. Patent Application Serial No. 10/572,502, filed on March 17, 2006, now U.S. Patent No. 8,163,306, issued on April 24, 2012, which is a U.S. national stage application filed under 35 U.S.C. § 371 from International Application Serial No. PCT/IN2004/000192, filed on June 30, 2004, and published as WO 2005/039481 on May 6, 2005, which claims the benefit of priority of India Application Serial No. 987/MUM/2003, filed on September 19, 2003, each of which is incorporated herein by reference in its entirety.--

Signed and Sealed this
Seventeenth Day of March, 2020

Andrei Iancu
*Director of the United States Patent and Trademark Office*